United States Patent
Bonaroti

(10) Patent No.: US 9,855,161 B1
(45) Date of Patent: Jan. 2, 2018

(54) SYSTEM AND METHOD FOR ASSISTING PLANTAR FLEXION FORCE AND CONTROLLING FORWARD TIBIAL PROGRESSION IN STANCE PHASE OF GAIT FOR STANCE STABILITY AND PROPULSION

(71) Applicant: Daniel Bonaroti, Phoenix, AZ (US)

(72) Inventor: Daniel Bonaroti, Phoenix, AZ (US)

(*) Notice: Subject to any disclaimer, the term of this patent is extended or adjusted under 35 U.S.C. 154(b) by 832 days.

(21) Appl. No.: 13/866,228

(22) Filed: Apr. 19, 2013

Related U.S. Application Data

(60) Provisional application No. 61/636,564, filed on Apr. 20, 2012.

(51) Int. Cl.
*A61F 5/01* (2006.01)

(52) U.S. Cl.
CPC .................. *A61F 5/0102* (2013.01)

(58) Field of Classification Search
CPC .. A61F 5/00; A61F 5/01; A61F 5/0102; A61F 5/0127; A61F 5/04; A61F 5/042; A61F 5/37
USPC .......... 128/846, 869, 882; 602/5, 12, 23, 26, 602/28, 60–62, 65
See application file for complete search history.

(56) References Cited

U.S. PATENT DOCUMENTS

| | | | |
|---|---|---|---|
| 2,525,237 A | 10/1950 | Park | |
| 2,847,991 A * | 8/1958 | Andrews | 602/28 |
| 3,073,305 A * | 1/1963 | Biggs, Jr. | A61F 5/0111 602/65 |
| 4,329,982 A | 5/1982 | Heaney | |
| 4,556,054 A * | 12/1985 | Paulseth | A61F 5/0111 602/27 |
| 4,955,370 A | 9/1990 | Pettine | |
| 5,088,480 A * | 2/1992 | Wang | 602/23 |
| 5,143,058 A * | 9/1992 | Luber et al. | 602/28 |
| 5,217,431 A * | 6/1993 | Toronto | A61F 13/065 602/27 |
| 5,376,068 A * | 12/1994 | Grifka | 602/27 |
| 5,843,010 A * | 12/1998 | Bodmer | 602/27 |
| 6,752,774 B2 | 6/2004 | Townsend | |
| 7,018,352 B2 * | 3/2006 | Pressman et al. | 602/27 |
| 8,382,694 B2 * | 2/2013 | Wenger | 602/23 |
| 8,425,440 B2 * | 4/2013 | DeToro et al. | 602/16 |
| 2001/0051780 A1 * | 12/2001 | Birmingham | 602/27 |
| 2009/0112140 A1 * | 4/2009 | Gaylord | A61F 5/0102 602/27 |
| 2009/0247923 A1 * | 10/2009 | Lundberg | A61F 5/0111 602/27 |
| 2012/0117821 A1 * | 5/2012 | Adams | A43B 3/0052 36/58.5 |

* cited by examiner

*Primary Examiner* — Kari Rodriquez
*Assistant Examiner* — Raymond E Harris

(57) ABSTRACT

A device for assisting with plantar flexion includes a calf component that secures to the lower leg, two attachment points located on the calf component, a heel and or forefoot attachment point, and a strap extending from an attachment point on the calf component to the heel and or forefoot attachment point. The strap of the device produces tension between the calf and the heel of the foot to assist with plantar flexion by either pulling the heel upwards or limiting forward tibial progression in stance to provide stance stability for that leg.

21 Claims, 7 Drawing Sheets

SYSTEM AND METHOD FOR ASSISTING PLANTAR FLEXION FORCE AND CONTROLLING FORWARD TIBIAL PROGRESSION IN STANCE PHASE OF GAIT FOR STANCE STABILITY AND PROPULSION

CROSS REFERENCE TO RELATED APPLICATION

This application claims priority to U.S. provisional application No. 61/636,564, entitled, "System and Device for Assisting Plantar Flexion," filed on Apr. 20, 2012, which is hereby incorporated by reference.

BACKGROUND OF THE INVENTION

Field of the Invention

This invention relates generally to the field of plantar flexion assistance. Plantar flexion occurs when the ankle is extended and the distal end of the foot moves away from the body, in other words, when the toes are pointed. Muscles that help in plantar flexion include among others: the gastrocnemius, the soleus, the plantaris, the tibialis posterior, the flexor hallucis posterior, and the flexor digitorium longus. When nerves, muscles, or tendons involved in plantar flexion are injured, a patient may have difficulty with plantar flexion. For example, weak plantar flexion muscles can make it difficult to walk. A patient, who has difficulty walking due to weakness in plantar flexion muscles or other injury, could benefit from a device worn to assist the patient in pointing their toes which in stance phase, controls the closed chain ankle dorsiflexion progression of the tibia during terminal stance creating necessary knee stability by limiting forward progression of the tibia that would cause knee flexion and knee buckling. The device also can assist in helping the person lift the heel in preswing, creating knee flexion at the appropriate time in pre swing and early swing phases of gait.

Description of Related Art

Various ankle foot orthoses (AFOs) and knee ankle foot orthoses (KAFOs) are available to stabilize the foot and ankle while in motion. Many of these orthotic devices are aimed at preventing foot drop or assisting with multiple gait problems in one device. Current devices for assisting with plantar flexion use undesirable materials or have extra features that are unnecessary for a patient with a specific need for plantar flexion assist without the need for dorsiflexion assist. These individuals are often more active and can not use a brace or splint that is dynamic enough and low profile enough to function in a highly active and at times athletic activity level.

So as to reduce the complexity and length of the Detailed Specification, and to fully establish the state of the art in certain areas of technology, Applicant(s) herein expressly incorporate(s) by reference all of the following materials identified in each numbered paragraph below.

U.S. Pat. No. 2,424,237 of Park et al. describes a foot drop brace that includes a plate extending from the heel portion of a shoe, a supporting arm connected to the plate, and a strap secured to the leg and to an upper end of the supporting arm. The device assists with foot drop, or dorsiflexion.

U.S. Pat. No. 4,329,982 of Heaney describes a device for assisting with foot drop having a leg attachment member, and elastomeric support strap secured to the leg attachment member, and a shoe with means for attaching the support strap near the forward portion of the shoe. The strap contracts to raise the toe of the foot to assist with dorsiflexion.

U.S. Pat. No. 4,955,370 of Pettine describes an Achilles tendon rehabilitation brace. The device includes a sole, side arms, a strap engaged at the calf area of the leg, and a tension adjustable spring attached at the toe area of the sole and at a side arm. The device is intended to urge and extend one's ankle into plantar flexion.

U.S. Pat. No. 6,752,774 of Townsend et al. describes a tension assisted knee ankle orthotic. The device includes a thigh shell with two bands holding the thigh shell to the thigh. The device further includes a below knee shell held to the lower leg with bands. The device also includes a foot plate connected to the below knee shell. Bands are connected at the joint of the foot plate and below knee shell to assist with dorsiflexion or plantar flexion.

Applicant(s) believe(s) that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

BRIEF SUMMARY OF THE INVENTION

The present invention provides among other things a plantar flexion assist device that assists a weak calf muscle during walking. The plantar flexion assist device provides stability for the knee and ankle to help treat orthopedic and neurologic injuries that affect plantar flexion.

In various representative aspects, the present invention may provide a plantar flexion assist device comprising a calf component configured to secure to a leg below a knee. The calf component may have a first attachment point on a first side of the calf component a second attachment point on a second side of the calf component, a strap comprising an elasticized material, a first end of the strap configured to attach to the first attachment point and a second end of the strap configured to attached to the second attachment point, and a heel component configured to secure to a foot. A midpoint of the strap may be configured to attach to the heel portion. The strap may be configured to create tension between the calf component and the heel component. There may be a first strap guide and a second strap guide coupled to the calf component, each strap guide creating a channel configured to house the strap such that the strap is constrained on each side of the leg. The first strap guide may extend from the first attachment point to the heel component and the second strap guide may extend from the second attachment point to the heel component. The first strap guide may cross over the second strap guide at a point on the back of the leg. The heel component may further comprises a removable shoe insert, the removable shoe insert having a loop extending upward from a heel end of the removable shoe insert. The heel component secures to the foot at the heel. The calf component may substantially cover the lower leg. The heel component may include the heel portion of the sole of the shoe. The heel component may include a shoe with a loop fixed to an upper heel area of the shoe. The calf component may include an elastic band. The calf component may include moldable plastic.

In other embodiments of the invention, the plantar flexion assist device may comprise a calf component configured to wrap around a leg below a knee, a strap comprising an elasticized material configured to attach to a medial and a lateral side of the calf component, and a heel component configured to secure to a foot and to couple to the strap. There may also be sock component comprising a cuff component, a leg component having a front side and a back side; and a foot component having a top side and a bottom side. The calf component may couple to the cuff component of the sock. The strap may couple to the leg component of the sock. The strap may couple to the foot component of the sock. The strap may be configured to create tension between the calf component and the foot component of the sock to create a plantar flexion force. The strap may be sewn to the leg portion of the sock. The sock may comprise elastic material. The heel component may further comprises a removable shoe insert, the removable shoe insert having a loop extending upward from a heel end of the removable shoe insert. The removable shoe insert may include moldable plastic. The loop may comprises a strap with a first end and a second end wherein the first end attaches to a first attachment point at the back of the removable shoe insert offset from the center of the heel and the second end attaches to the removable shoe insert heel at a second point at the back of the removable shoe insert heel offset from the center wherein the heel of the foot rests between the first and second attachment points. The plantar flexion assist device may further comprise a first strap guide and a second strap guide coupled to the calf component, each strap guide creating a channel configured to house the strap such that the strap is constrained on each side of the leg.

In still another embodiments, the plantar flexion assist device may comprise a lower leg belt configured to wrap around a lower leg and having at least two attachment loops, an elastic strap configured to attach to the two attachment loops, and a shoe attachment configured to receive the elastic strap at a heel of a shoe.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figure 1:
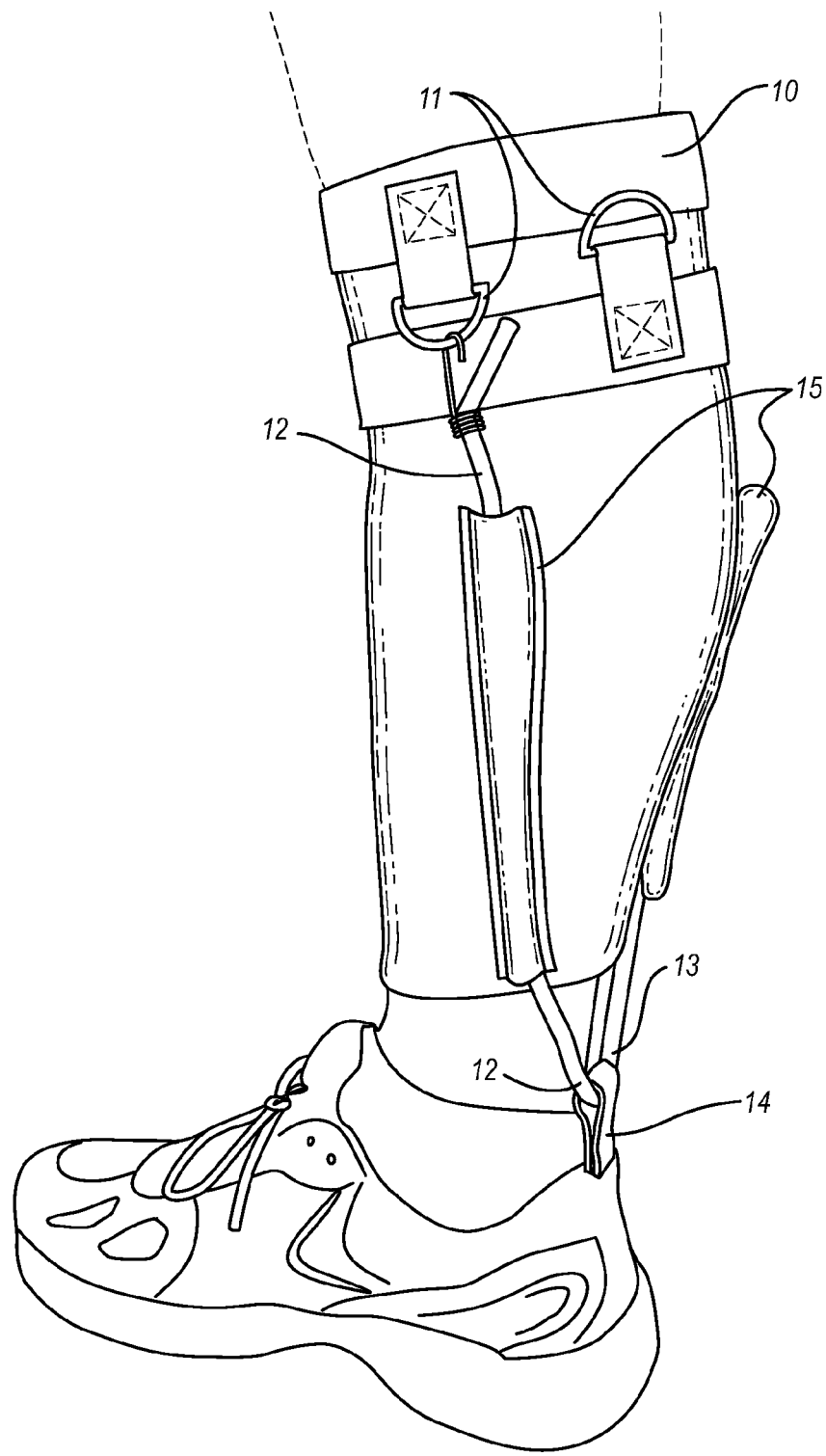
FIG. 1 depicts a perspective view of a device for assisting plantar flexion, according to one embodiment of the present invention.

In one application of the invention, referring now to FIG. 1, a device according to various aspects of the invention is depicted from a perspective view. In the embodiment pictured in FIG. 1, the device for assisting with plantar flexion comprises a calf component 10, at least two attachment points 11, and an elastic strap 12. The elastic strap 12 is configured to couple to a heel attachment point 14, which is also at approximately the midpoint 13 of the strap 12. The heel attachment point 14 may be a part of a shoe, such as a loop on the heel portion of a shoe. The calf component 10 may also comprise channels 15 to house the strap 12 on each side of the lower leg.

The strap 12 couples to the calf component 10 and the heel attachment point 14 to create a force on the heel area of the foot that pulls the heel upwards. The force of the strap 12 pulling on the heel attachment point 14 allows a patient to extend their foot in plantar flexion with less muscle exertion than would normally be needed without the assistance of the device. While wearing the device and walking, a plantar flexion force is created, controlling forward progression of the tibia and allowing a patient with weak plantar flexion muscles to walk with less effort.

The calf component 10 provides a securing point for the strap 12 to couple to. The calf component 10 may be an elastic band or strap, webbing, moldable plastic, a sleeve, or any material that can secure tightly, but comfortably, to the low leg below the knee. In the present embodiment, the calf component 10 includes an elastic material in the form of a sleeve and webbing. The calf component 10 may have two or more attachment points 11. The attachment points 11 may be loops, rings, carabineers, extensions of the calf component 10 material, or other attachment devices that can both attach to the calf component 10 and also provide a place for the straps 12 to couple to. In the present embodiment, the attachment points 11 are metal rings sewn into webbing of the calf component 10.

The strap 12 couples to the calf component 10 at the attachment points 11. The strap 12 also attaches to a heel attachment point 14 at approximately a midpoint 13 of the strap 12. The strap 12 may be any elastic material, such as rubber, latex, elastic band, braided shock cord, bungee cord, woven elastic, or the like. In one embodiment of the invention, the strap 12 includes braided elastic cord. The strap 12 provides tension between the calf component 10 and the heel attachment point 14. Each end of the strap 12 couples to the calf component 10 at the attachment points 11. The ends of the strap may be configured to hook, tie, clasp, clip, or otherwise connect to the attachment points 11 of the calf component 10. In the present embodiment, the ends of the strap 12 include hooks.

In the present embodiment, one strap 12 is used to create the force to pull the heel portion of the foot upwards. Alternatively, more than one strap 12 can be used to accomplish this force. For example, more straps could be added if more force was needed for effective assistance of plantar flexion.

The calf component 10 may comprise channels 15 in the embodiment of calf component 10 that includes a sleeve covering part of the lower leg below the knee. The channels 15 may provide a housing for part of the strap 12. The channels 15 are located on each side of the calf component 10, a medial side and a lateral side. The channels 15 run along the length of the calf component 10, from the upper portion of the calf component 10 to the lower portion of the calf component 10. The channels 15 direct the strap 12 into a secure location where the strap 12 cannot catch on clothing or otherwise get in the way of other activities. The channels 15 also ensure that the strap 12 stay oriented in a position that provides the proper direction of force created by the strap 12.

The straps 12 couple to a heel attachment point 14 in order to provide an upwards force at the heel of a patient's foot. The heel attachment point 14 may be an extension of a shoe, such as the shoe loop depicted in FIG. 1. Alternatively, the heel attachment point 14 may be an adapted shoe insert or it may interface with the inner or outer sole of the shoe itself. The shoe insert may be molded plastic with two holes that a strap 12 can be threaded through. Or, the shoe insert may have an attached loop that is configured to receive a strap 12.

Figure 2:
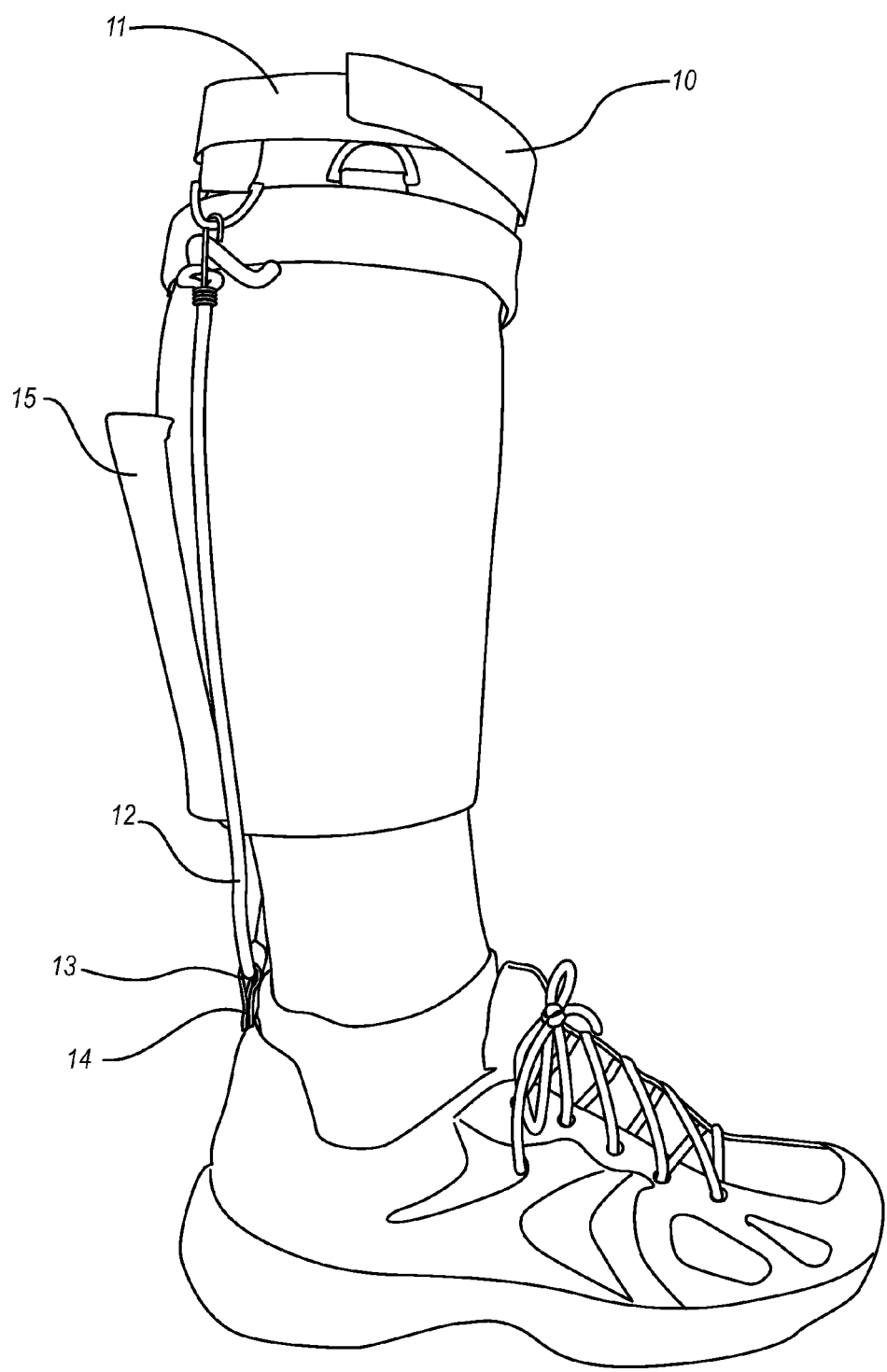
FIG. 2 depicts a side view of a device for assisting plantar flexion, according to one embodiment of the present invention.

An embodiment of the device is shown in FIG. 2 in side view. Similar to FIG. 1, FIG. 2 shows the calf component 10 that extends from just below the knee to a point on the lower leg above the ankle. In the view in FIG. 2, an attachment point 11 is coupled to the lateral side of the calf component 10. The strap 12 couples to the attachment point 11 and extends down to the heel attachment point 14. The strap 12, in one embodiment, may couple to the heel attachment point 14 at a midpoint 13 of the strap 12. In the embodiment in FIG. 2, the strap 12 is not housed within the channel 15. FIG. 2 shows how the strap 12 can couple to the attachment point 11 and the heel attachment point 14 when the channels are not used.

Figure 3:
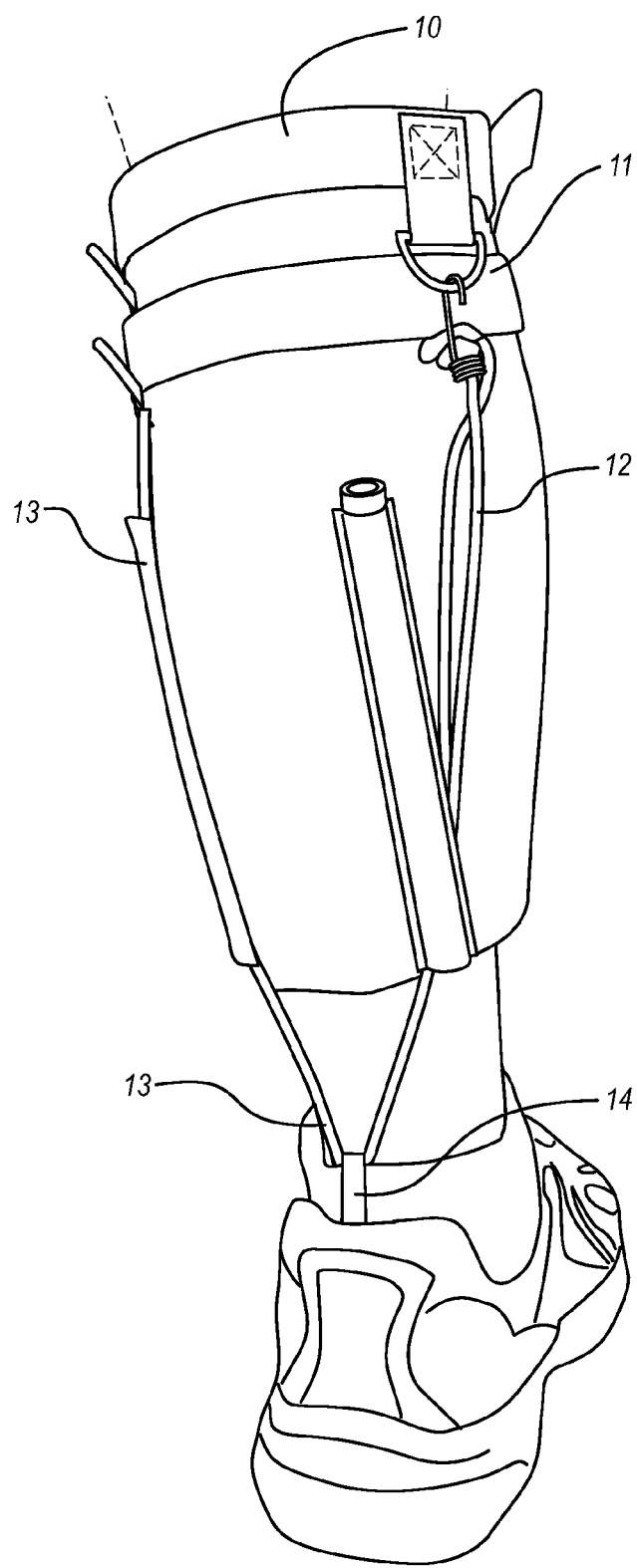
FIG. 3 depicts a rear view of a device for assisting plantar flexion, according to one embodiment of the present invention.

The embodiment of the device shown in FIG. 2 is also shown in FIG. 3 from a posterior angle or rear view. In FIG. 3, the device shows strap 12 extending from a medial attachment point 11 on the calf component 10 down the lower leg to the heel attachment point 14 at the midpoint of the strap 12. The strap then extends from the heel attachment point 14 up the lower leg to a lateral attachment point 11 on the calf component 10. In the embodiment of FIG. 3, the strap 12 does not thread completely through a channel 15. In an alternative embodiment, the strap 12 threads downward through a channel 15 located along the medical portion of the calf component 10, and then threads upwards through a channel 15 located along the lateral portion of the calf component 10.

Figure 4:
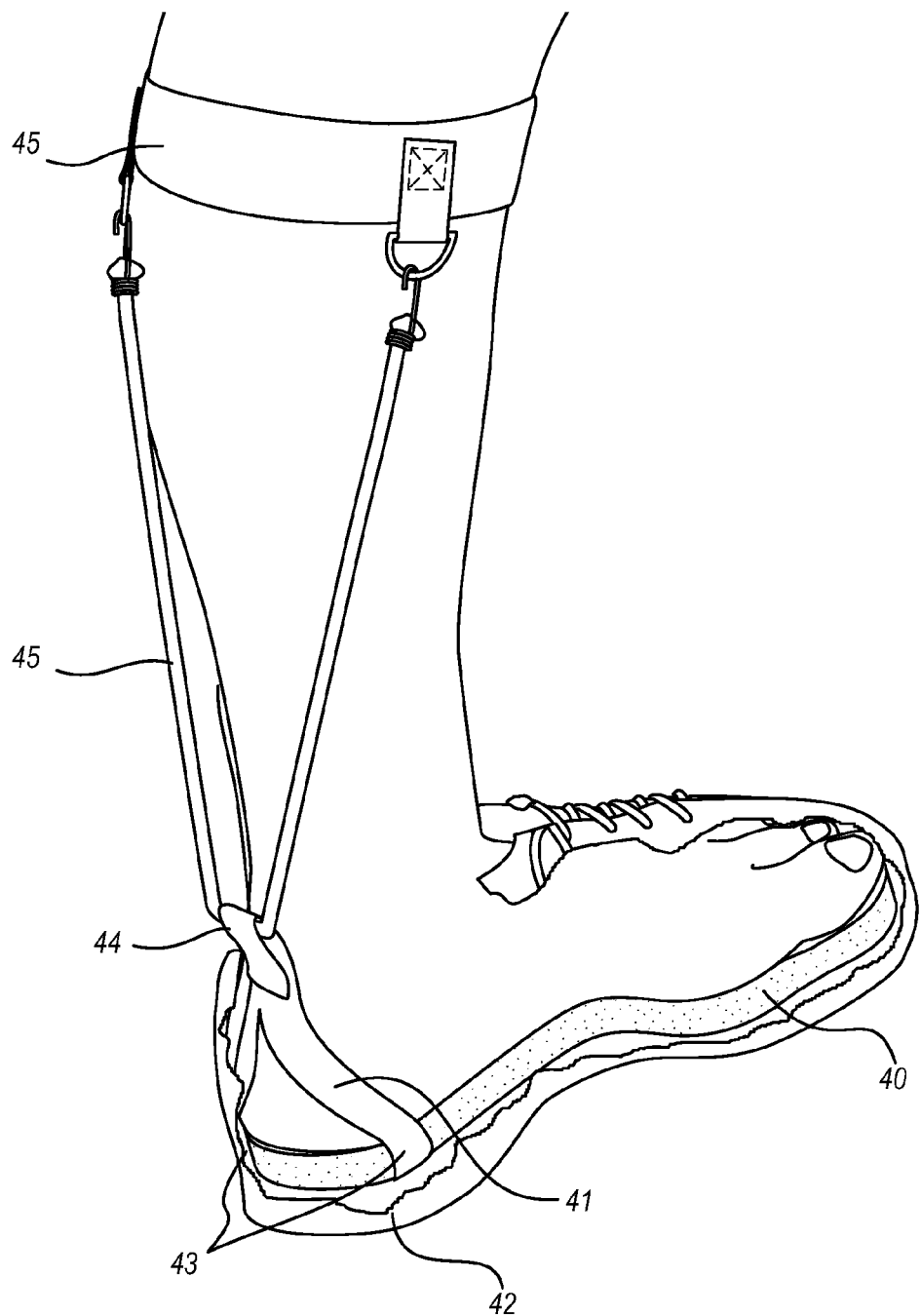
FIG. 4 depicts a perspective side view of a shoe insert and heel attachment portion of an implementation of the plantar flexion assist device.

FIG. 4 shows a perspective view of a shoe insert and heel attachment portion according to one implementation of the plantar flexion assist device. The device may adapt to a shoe by providing a heel attachment portion as a shoe insert. FIG. 4 depicts a shoe insert 40 that is adapted for a patient's shoe. The shoe insert 40 may be any type of shoe insert that can be adapted to receive a heel attachment. The shoe insert 40 may be molded plastic, or the shoe insert 40 may be off-the-shelf and adapted for use in this device. In the embodiment shown in FIG. 4, a lower portion 42 of a first loop 41 may couple to the shoe insert 40 at attachment points 43 on the side of the shoe insert 40 at the back of the heel laterally offset from the center of the heel and at another attachment point on the opposite side of the heel at the back of the heel laterally offset from the center of the heel. In other embodiments the lower portion of the loop portion 42 may couple to the shoe insert underneath the back heel of the shoe insert. A second loop portion 44 may attach to the first loop 41. The second loop portion 44 may receive a strap 45 used to create the necessary force between the shoe insert 40 and the calf component 46.

Figure 5:
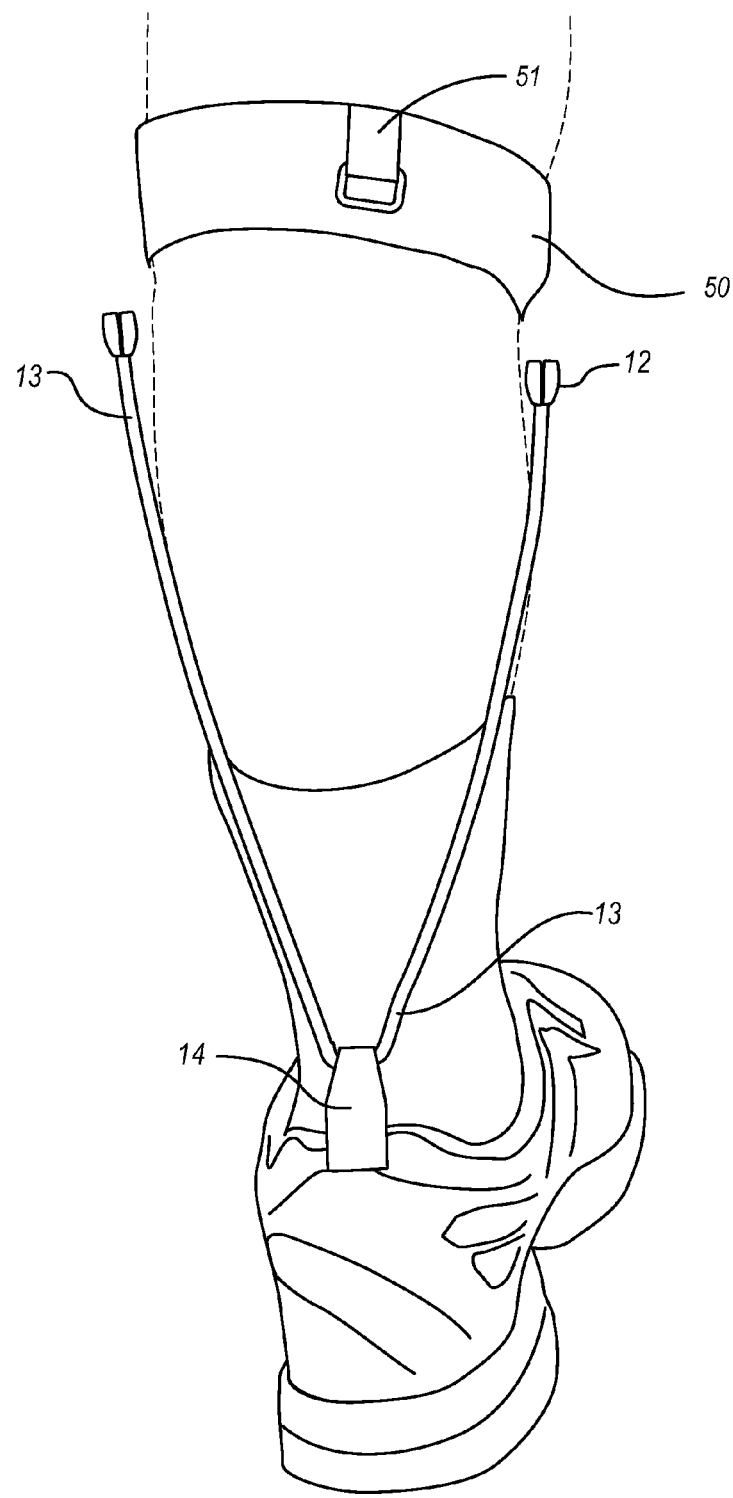
FIG. 5 depicts a rear view of an implementation of a plantar flexion assist device having a reduced calf component.

FIG. 5 depicts a rear view of an implementation of the plantar flexion assist device having an alternative design of the calf component. In the embodiment in FIG. 5, the calf component 50 comprises a smaller surface area of material. The calf component 50 comprises a band of elastic material having at least two attachment points 51. Similar to other embodiments of this device, the strap 12 provides tension between the calf component 10 and the heel attachment point 14. The strap reaches the heel attachment point 14 at about the midway point 13 of the strap 12. The device provides tension through the strap 12 as it is attached to the calf component 50, which provides a first and second anchor for the strap at attachment points 51, and the heel attachment point 14 which provides the third anchor for the strap. The tension provided by the strap 12 between the calf and the heel and allows the device to left the heel and provide plantar flexion assistance.

Figure 6:
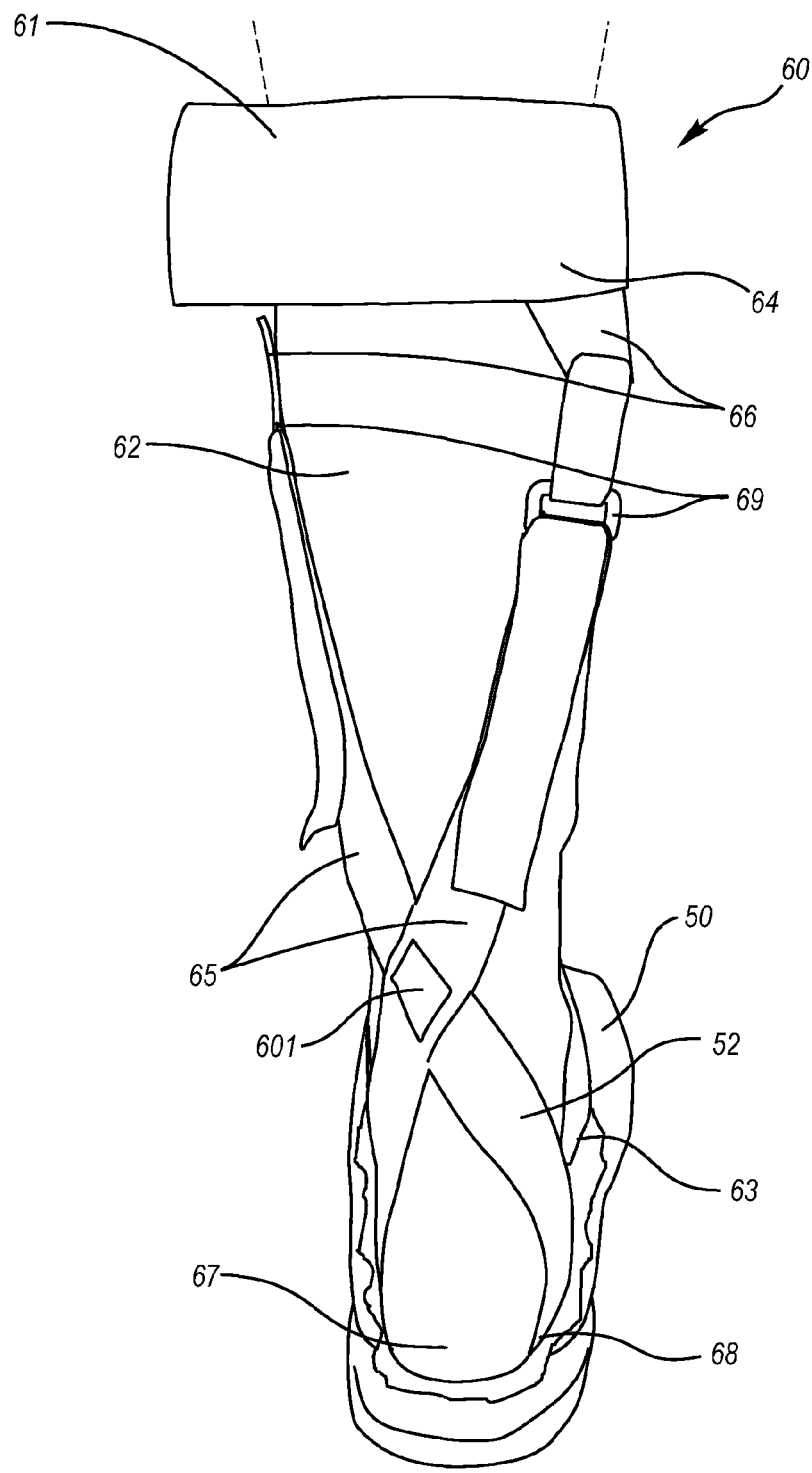
FIG. 6 depicts a rear view of an embodiment of the implementation of the plantar flexion assist device integrated into a sock.

In another application of the invention, referring now to FIG. 6, a further embodiment according to various aspects of the invention is depicted from a rear view. In the embodiment pictured in FIG. 6, the device for assisting with plantar flexion is integrated into a sock 60 comprising a cuff component 61, a leg component 62, and a foot component 63. A calf component 64 is integrated into the cuff component of the sock 60. The calf component 64 may comprise reinforced material sewn into the cuff of the sock or it may use the same material as the cuff of the sock. Elastic straps 65 attach to calf component 64 at attachment points 66 and couples the calf component 64 to a heel component 67 that is integrated into the foot component 63 of the sock 60. The elastic straps 65 may be sewn into the leg component 62 of the sock 60 or the elastic straps 65 may comprise elastic material fabricated as part of the leg component 62 of the sock 60. The heel component 66 may comprise reinforced material sewn into the heel of the sock 60. There may be at least one attachment point 66 coupled to the calf component 64, and one or more elastic straps 62 integrated into the sock 60. The elastic straps may be a single straps or separate straps, each configured with a first end connected to the calf component 64 at attachment points 66 and a second end connected to the heel component 66 at attachment point 68.

The elastic straps 65 couples to the calf component 64 and the heel attachment point 68 to create a force on the heel area of the foot that pulls the heel upwards. The force of the straps 65 pulling on the heel attachment point 68 allows a patient to extend their foot in plantar flexion with less muscle exertion than would normally be needed without the assistance of the device. While wearing the device and walking, the foot is pulled into plantar flexion and a patient with weak plantar flexion muscles can walk easier.

The calf component 64 provides one or more securing points 66 that couple to the straps 65. The calf component 64 may be an elastic band or strap, webbing, moldable plastic, a sleeve, or any material that can be integrated into the sock 60. In the present embodiment, the calf component 64 includes an elastic material in the form of a sleeve and webbing. The calf component 64 may have two or more attachment points 66. The cuff portion 61 may have plastic, fabric or metal attachment rings to allow for adjustment of the elastic straps or other attachment devices that can both attach to the calf component 61 and also provide a place for the straps 65 to couple to the calf component 61. In the present embodiment, the attachment points 66 are nylon fasteners sewn into webbing of the calf component 61. Alternatively gussets, rings, or other suitable attachment devices may be used to fasten the calf component 61 to straps 65 at attachment points 66. The attachment devices may be sewn into the sock 60 at attachment points 66. The attachment points 66 may comprise plastic, fabric, or metal rings. The attachment points 66 may couple to strap adjusters 69 to adjust the tension on the strap 65 between the heel component 68 and the calf component 66.

The straps 65 couple to the calf component 64 at the attachment points 66. The straps 65 also attach to a heel attachment point 68 at approximately a midpoint of the straps 65. The straps 65 may be any elastic material, such as rubber, latex, elastic band, braided shock cord, bungee cord, woven elastic, or the like. In one embodiment of the invention, the straps 65 include braided elastic cord. The straps may be flat elastic/fabric combination, rubber tubing or rubber cords or nylon cords. The straps 65 provide tension between the calf component 64 and the heel attachment point 68. Each end of the straps 65 couple to the calf component 64 at the attachment points 66. The ends of the straps 65 may be configured to connect to the attachment points 66 of the calf component 60. In the present embodiment, the ends of the straps 65 may loop through strap adjusters 69. In some embodiments the straps 65 may cross in an x pattern at point 601 to provide stability and consistent pull patterns between the calf component via sewing, velcro, tubing, plastic or metal clasps.

In the present embodiment, two straps 65 are used to create the force to pull the heel portion of the foot upwards. Alternatively, one strap or multiple straps 65 may be used to create this force. For example, more straps could be added if more force was needed for effective assistance of plantar flexion. The straps 65 may be crisscrossed with a cross over point 601 or may run parallel to the sock.

Figures 7, 8:
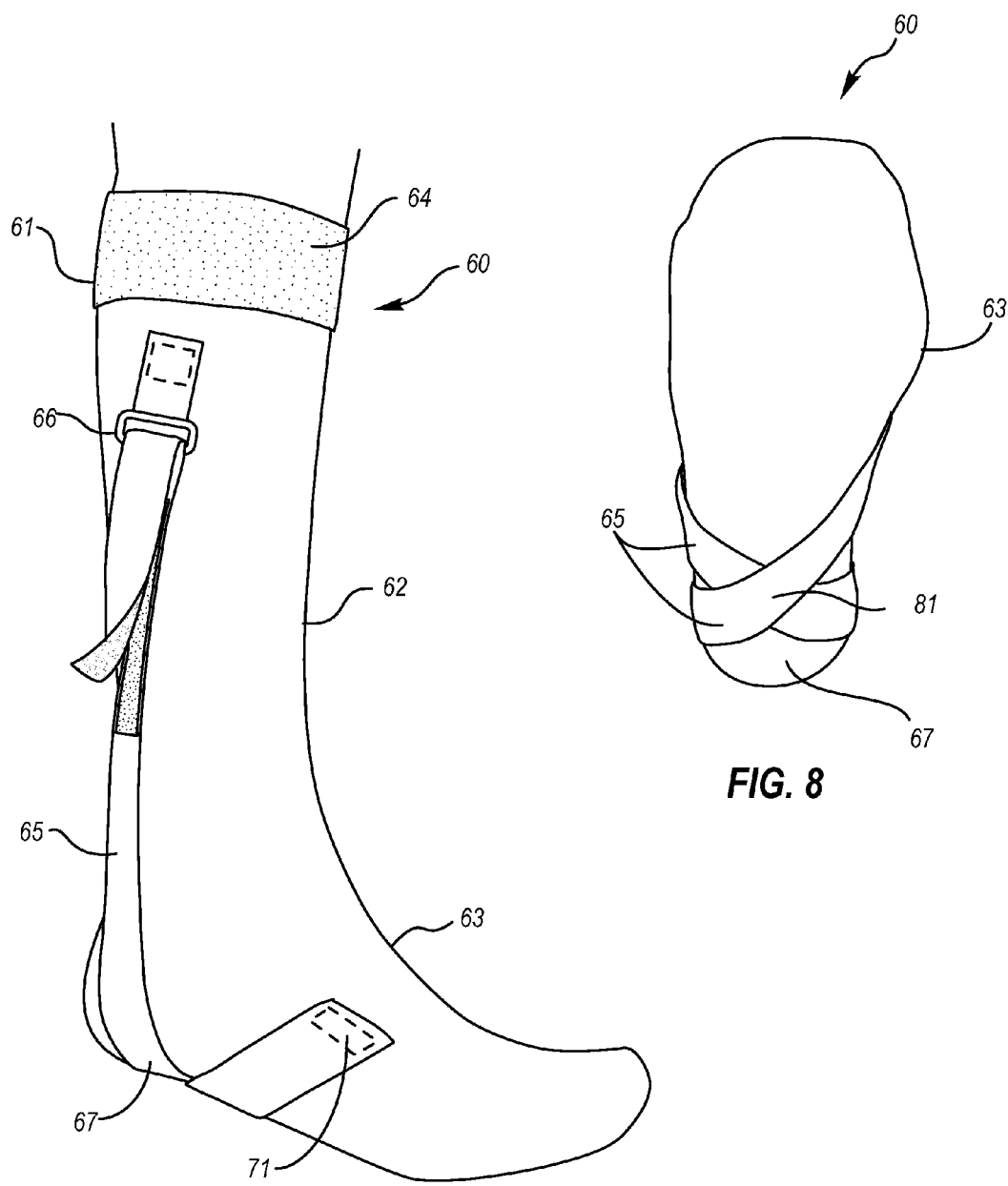
FIG. 7 depicts a side view of an embodiment of the implementation of the plantar flexion assist device integrated into a sock.
FIG. 8 depicts a side view of an embodiment of the implementation of the plantar flexion assist device integrated into a sock.

Referring now to FIG. 7, the sock 60 of FIG. 6 is depicted from a side view. In the embodiment pictured in FIG. 7, the device for assisting with plantar flexion is integrated into a sock 60 comprising a cuff component 61, a leg component 62, and a foot component 63. A calf component 64 is integrated into the cuff component of the sock 60. The calf component 64 may comprise reinforced material sewn into the cuff of the sock or it may use the same material as the cuff of the sock. Elastic strap 65 attaches to calf component 64 at attachment points 66 and couples the calf component 64 to a heel component 67 that is integrated into the foot component 63 of the sock 60. The elastic strap 65 may be sewn into the leg component 62 of the sock 60 or the elastic strap 65 may comprise elastic material fabricated as part of the leg component 62 of the sock 60. The heel component 67 may comprise reinforced material sewn into the heel of the sock 60. There may be at least one attachment point 66 coupled to the calf component 64, and one or more elastic straps 65 integrated into the sock 60. The straps 65 wrap underneath the heel component 67 and attach to the foot component at points 71 on the sides of the foot component 63 of the sock 60.

Referring now to FIG. 8, the sock 60 of FIG. 6 is depicted from a bottom view. FIG. 8 shows the straps 65 wrap around the bottom of the foot component 63 crossing at a point 81 on the outer surface of the heel component 67. The straps 65 may be sewn into the leg component of the sock 60 and sewn into the heel component 67 of the sock 60.

I claim:

1. A plantar flexion assist device, comprising:
   a calf component configured to secure to a leg below a knee, the calf component having a first attachment point on a first side of the calf component and a second attachment point on a second side of the calf component;
   a heel component configured to secure to a foot a strap comprising an elasticized material, a first end of the strap configured to attach to the first attachment point, a second end of the strap configured to attach to the second attachment point, and a midpoint of the strap configured to attach to the heel component such that the strap creates tension between the calf component and the heel component;
   a first strap guide coupled to the calf component and extending from the first attachment point to the heel component and a second strap guide coupled to the calf component and extending from the second attachment point to the heel component, each strap guide creating a channel configured to house the strap such that the strap is constrained on each side of the leg.

2. The plantar flexion assist device of claim 1, wherein the heel component further comprises a removable shoe insert, the removable shoe insert having a loop extending upward from a heel end of the removable shoe insert.

3. The plantar flexion assist device of claim 1, wherein the heel component is configured to secure to the foot at a heel.

4. The plantar flexion assist device of claim 1, wherein the calf component is configured to substantially cover a lower leg.

5. The plantar flexion assist device of claim 1, wherein the heel component includes comprises the heel portion of the sole of a shoe.

6. The plantar flexion assist device of claim 1, wherein the heel component comprises a shoe with a loop fixed to an upper heel area of the shoe.

7. The plantar flexion assist device of claim 1, wherein the calf component comprises an elastic band.

8. The plantar flexion assist device of claim 1, wherein the calf component comprises moldable plastic.

9. A plantar flexion assist device, comprising:
   a calf component configured to wrap around a leg below a knee;
   a strap comprising an elasticized material configured to attach to a medial and a lateral side of the calf component;
   a sock component comprising:
     a cuff component;
     a leg component having a front side and a back side; and a foot component having a top side and a bottom side and comprising a heel component configured to secure to a foot and to couple to the strap;

wherein:

the calf component is coupled to the cuff component of the sock component;

the strap is coupled to the leg component of the sock component;

the strap is coupled to the foot component of the sock component; and wherein the strap is configured to create tension between the calf component and the foot component of the sock component to create a plantar flexion force; and wherein the strap is sewn to the leg component of the sock component.

10. The plantar flexion assist device of claim 9, wherein the heel component further comprises a removable shoe insert, the removable shoe insert comprising a loop extending upward from a heel end of the removable shoe insert.

11. The plantar flexion assist device of claim 10, wherein the removable shoe insert comprises moldable plastic.

12. The plantar flexion assist device of claim 10, wherein the loop comprises a strap with a first end and a second end wherein the first end attaches to a first attachment point at the back of the removable shoe insert offset from the center of the heel and the second end attaches to the removable shoe insert heel at a second point at the back of the removable shoe insert heel offset from the center wherein the heel of the foot is configured to rest between the first and second attachment points.

13. The plantar flexion device of claim 9 wherein the sock component comprises elastic material.

14. The plantar flexion assist device of claim 9, further comprising a first strap guide and a second strap guide coupled to the calf component, each strap guide creating a channel configured to house the strap such that the strap is constrained on each side of thea leg.

15. A plantar flexion assist device, comprising:

a calf component configured to secure to a leg below a knee, the calf component having a first attachment point on a first side of the calf component and a second attachment point on a second side of the calf component, a strap comprising an elasticized material, a first end of the strap configured to attach to the first attachment point and a second end of the strap configured to attached to the second attachment point;

a heel component configured to secure to a foot, wherein a midpoint of the strap is configured to attach to the heel component and wherein the strap is configured to create tension between the calf component and the heel component; and a first strap guide and a second strap guide coupled to the calf component, each strap guide creating a channel configured to house the strap such that the strap is constrained on each side of a leg wherein the heel component further comprises a removable shoe insert, the removable shoe insert comprising a loop extending upward from a heel end of the removable shoe insert.

16. The plantar flexion assist device of claim 15, wherein the first strap guide extends from the first attachment point to the heel component and the second strap guide extends from the second attachment point to the heel component.

17. The plantar flexion assist device of claim 16, wherein the first strap guide is configured to cross over the second strap guide at a point on the back of a leg.

18. The plantar flexion assist device of claim 15, wherein the heel component is configured to secure to the foot at a heel.

19. The plantar flexion assist device of claim 15, wherein the calf component is configured to substantially cover a lower leg.

20. The plantar flexion assist device of claim 15, wherein the calf component comprises an elastic band.

21. The plantar flexion assist device of claim 15, wherein the calf component comprises moldable plastic.

* * * * *